(12) United States Patent
Shah et al.

(10) Patent No.: US 9,820,991 B2
(45) Date of Patent: Nov. 21, 2017

(54) PHARMACEUTICAL COMPOSITION COMPRISING BRINZOLAMIDE

(71) Applicant: SENTISS PHARMA PVT. LTD., Gurgaon (IN)

(72) Inventors: Mandar Shah, Haryana (IN); Divya Pandit, Himachal Pradesh (IN); Deepak Bahri, Haryana (IN)

(73) Assignee: SENTISS PHARMA PRIVATE LIMITED, New Delhi (IN)

( * ) Notice: Subject to any disclaimer, the term of this patent is extended or adjusted under 35 U.S.C. 154(b) by 0 days.

(21) Appl. No.: 15/058,795

(22) Filed: Mar. 2, 2016

(65) Prior Publication Data

US 2016/0175317 A1   Jun. 23, 2016

Related U.S. Application Data (63) Continuation-in-part of application No. PCT/IB2015/050511, filed on Jan. 23, 2015, and a continuation-in-part of application No. PCT/IB2014/065806, filed on Nov. 5, 2014.

(30) Foreign Application Priority Data

Nov. 8, 2013   (IN) .......................... 3298/DEL/2013
Jan. 24, 2014   (IN) .......................... 223/DEL/2014

(51) Int. Cl.

| A61K 31/542 | (2006.01) |
| A61K 47/02 | (2006.01) |
| A61K 47/18 | (2017.01) |
| A61K 47/26 | (2006.01) |
| A61K 47/32 | (2006.01) |
| A61K 47/34 | (2017.01) |
| A61K 9/00 | (2006.01) |
| A61K 9/08 | (2006.01) |
| A61K 9/10 | (2006.01) |

(52) U.S. Cl.
CPC .......... *A61K 31/542* (2013.01); *A61K 9/0048* (2013.01); *A61K 9/08* (2013.01); *A61K 9/10* (2013.01); *A61K 47/02* (2013.01); *A61K 47/183* (2013.01); *A61K 47/186* (2013.01); *A61K 47/26* (2013.01); *A61K 47/32* (2013.01); *A61K 47/34* (2013.01)

(58) Field of Classification Search
None
See application file for complete search history.

(56) References Cited

U.S. PATENT DOCUMENTS

| 5,378,703 | A |  | 1/1995 | Dean et al. |  |
| 5,665,331 | A | * | 9/1997 | Bagchi | A61K 9/145 424/1.29 |
| 6,071,904 | A | * | 6/2000 | Ali | A61K 9/0048 514/222.8 |
| 2009/0098207 | A1 | * | 4/2009 | Malakhov | A61K 9/5089 424/489 |
| 2013/0053374 | A1 | * | 2/2013 | Inoue | A61K 31/138 514/226.5 |

FOREIGN PATENT DOCUMENTS

| EP | 0 941 094 B1 | 12/2001 | |
| EP | 0 527 801 B1 | 7/2002 | |
| EP | 2 394 637 | 12/2011 | |
| IN | WO 2012053011 A2 * | 4/2012 | .......... A61K 9/0048 |
| WO | WO 98/25620 A1 | 6/1998 | |

\* cited by examiner

*Primary Examiner* — Robert A Wax
*Assistant Examiner* — William Craigo
(74) *Attorney, Agent, or Firm* — Greenblum & Bernstein, P.L.C.

(57) ABSTRACT

The present invention provides an improved novel process of manufacturing a sterile, ophthalmic pharmaceutical suspension comprising an active ingredient(s) such as carbonic anhydrase inhibitors (CAIs) wherein the said process involves solubilization, followed by controlled precipitation of carbonic anhydrase inhibitors of the right particle size, e.g., less than 10 micron, preferably less than 5 micron ($D_{90}$) by varying pH with a little or no homogenization. Said process further does not require the use of any special equipment such as ball mill, milling bottle and/or jet mill. This newly improved process is simple, cost effective and efficient.

14 Claims, 3 Drawing Sheets

PHARMACEUTICAL COMPOSITION COMPRISING BRINZOLAMIDE

CROSS-REFERENCE TO RELATED APPLICATIONS

This application is a continuation-in-part of International Application No. PCT/IB2014/065806, filed Nov. 5, 2014, which claims priority to Indian Application No. 3298/DEL/2013, filed Nov. 8, 2013; and International Application No. PCT/IB2015/050511 filed Jan. 23, 2015, which claims priority to Indian Application No. 223/DEL/2014, filed Jan. 24, 2014; all of which are incorporated by reference herein in their entireties. To the extent there may be any discrepancy between the priority documents (on the one hand) and the present specification (on the other hand), the present specification controls.

FIELD OF THE INVENTION

The present invention relates to an improved novel process of manufacturing sterile, ophthalmic pharmaceutical suspensions comprising non-sterile active ingredient(s) such as carbonic anhydrase inhibitors (CAIs), specifically, non-sterile brinzolamide wherein the said process involves solubilization, followed by controlled precipitation of carbonic anhydrase inhibitors of the right particle size, i.e., less than 10 micron, preferably less than 5 micron ($D_{90}$) by varying pH with a little or no homogenization.

The present invention further does not require the use of any special equipment such as ball mill, milling bottle and/or jet mill.

The sterile ophthalmic pharmaceutical suspensions are useful in the treatment of elevated intraocular pressure in persons suffering from ocular hypertension or primary open angle glaucoma.

BACKGROUND OF THE INVENTION

Brinzolamide is a carbonic anhydrase inhibitor used to lower intraocular pressure in patients with ocular hypertension or open-angle glaucoma. Brinzolamide is chemically (R)-(+)-4-Ethylamino-2-(3-methoxypropyl)-3,4-dihydro-2H-thieno [3,2-e]-1,2-thiazine-6-sulfonamide-1,1-dioxide and has the empirical formula $C_{12}H_{21}N_3O_5S_3$. Brinzolamide has a molecular weight of 383.5 and a melting point of about 125-127° C.

This compound is disclosed in U.S. Pat. No. 5,378,703 (Dean, et al.). The compound is also disclosed in European patent EP 527801. U.S. Pat. No. 6,071,904 discloses processes for preparation of brinzolamide ophthalmic composition.

Brinzolamide ophthalmic suspension is developed and marketed by Alcon Laboratories Inc. in United States under the brand name AZOPT® (Brinzolamide ophthalmic suspension 1%). Brinzolamide is indicated for lowering elevated intra-ocular pressure (IOP) in patients with open-angle glaucoma or ocular hypertension (OHT).

Various methods have been disclosed in the prior for the preparation of brinzolamide ophthalmic suspension. International patent application WO 98/25620 teaches that conventional sterilization methods cannot be employed in the manufacture of suspensions comprising brinzolamide since the compound recrystallizes at autoclaving temperatures forming large needle-type crystals.

According to WO 98/25620, also dry heat sterilization is not suitable since it causes melting of the material.

EP0941094 discloses a process for making brinzolamide suspension by autoclaving of concentrated slurry of brinzolamide in milling bottle, ball milling of the hot slurry, and then adding the slurry to the rest of the ingredients.

EP2394637 discloses a process for sterilizing brinzolamide suspensions using gamma irradiation or ethylene oxide.

In these cited references procedures, the use of a typical ball milling process to reduce particle size of ophthalmic drugs in aqueous suspensions is not desirable for several reasons. Firstly, the ball-milling process and parameters must be carefully controlled in order to ensure adequate particle size reduction.

The cited reference discloses autoclaving of the slurry of brinzolamide and surfactant and further ball milling the slurry. However, the drawback associated with this method is that it requires a milling bottles in which the slurry of brinzolamide could initially be autoclaved and then ball milled for further size reduction of needle shaped crystals of brinzolamide that are formed during autoclaving leading to wastage, expensive, time consuming and non-reproducible process. Furthermore the use of expensive instruments adds to the cost of production.

The inventors of the present invention have developed an improved novel process for preparation of sterile ophthalmic pharmaceutical suspension. The inventors of the present invention have surprisingly invented a cost effective, easily reproducible process with minimal use of equipment and least complex technology for manufacturing a sterile ophthalmic suspension comprising non-sterile brinzolamide wherein the said novel process involves solubilization, followed by controlled precipitation of carbonic anhydrase inhibitors of the right particle size, i.e., less than 10 micron, preferably less than 5 micron ($D_{90}$) by varying pH with a little or no homogenization.

The improved novel process further does not require the use of any specific equipment such as ball mill, milling bottle and/or jet mill.

This process ameliorates the drawbacks associated with cited references methods for preparation of brinzolamide ophthalmic suspension.

Objects of the Present Invention

The main object of the present invention is to provide an improved novel process of manufacturing a sterile, ophthalmic pharmaceutical suspension comprising carbonic anhydrase inhibitors (CAIs), such as brinzolamide and/or pharmaceutically acceptable excipients thereof wherein the said novel process involves solubilization, followed by controlled precipitation of brinzolamide of the right particle size, i.e., less than 10 micron, preferably less than 5 micron ($D_{90}$) by varying pH with a little or no homogenization.

Another object of the present invention is to provide an improved novel process which is simple, efficient, easily reproducible and cost effective.

Another object of the present invention is to provide a novel process for manufacturing ophthalmic pharmaceutical formulation wherein the said process preferably doesn't require the use of any special equipment such as ball mill, milling bottle and/or jet mill (though optional use thereof does not take one outside the present invention), and may optionally require the use of mild homogenization.

Another object of the present invention is to provide an improved novel process of manufacturing a sterile, ophthalmic pharmaceutical suspension comprising carbonic anhydrase inhibitors (CAIs), such as brinzolamide and a beta-blocker, optionally with pharmaceutically acceptable excipients thereof.

Yet another object of the present invention is to provide a sterile ophthalmic pharmaceutical suspension as disclosed herein the specification that are useful in the treatment of elevated intraocular pressure in patients with ocular hypertension or open angle glaucoma.

SUMMARY OF THE INVENTION

The present invention provides a simple, cost effective and efficient novel process of manufacturing a sterile brinzolamide ophthalmic suspension wherein the said novel process involves solubilization, followed by controlled precipitation of brinzolamide of the right particle size, e.g., less than 15 microns, less than 10 microns, or more preferably less than 5 microns ($D_{90}$) by varying pH with a little or no homogenization.

The present invention provides a novel process of manufacturing a sterile, ophthalmic pharmaceutical suspension comprising non-sterile active ingredient(s) such as non-sterile carbonic anhydrase inhibitors (CAIs) wherein the process doesn't require the use of any special equipment such as ball mill, milling bottle and/or jet mill. Another embodiment of the present invention is to provide an efficient and economic novel process of manufacturing a sterile brinzolamide ophthalmic pharmaceutical suspension compared to ball milled process wherein the present improved process can minimize or prevent the suspended drug particles from forming aggregates.

Further embodiment of the present invention provides a process of manufacturing a sterile, ophthalmic pharmaceutical suspension comprising non-sterile active ingredient(s) such as non-sterile carbonic anhydrase inhibitors (CAIs) wherein the compositions are formulated optionally with a pharmaceutically acceptable preservative such that the suspension may be formulated both as a unit-dose as well as multi-dose composition.

Furthermore in an embodiment, the manufacturing process of the present invention surprisingly reduces the generation of Impurity A wherein the reduction of Impurity A will enhance the shelf-life of the product thereby increases the stability of the present invention.

Another embodiment of the present invention is to provide a process of manufacturing a sterile brinzolamide ophthalmic pharmaceutical suspension which ameliorates one or more drawbacks of the reference processes.

The sterile ophthalmic pharmaceutical suspensions as prepared by the novel process of the present invention as disclosed herein the specification are useful in the treatment of elevated intraocular pressure in patients with ocular hypertension or open-angle glaucoma.

DETAILED DESCRIPTION OF THE INVENTION

Figure 1:
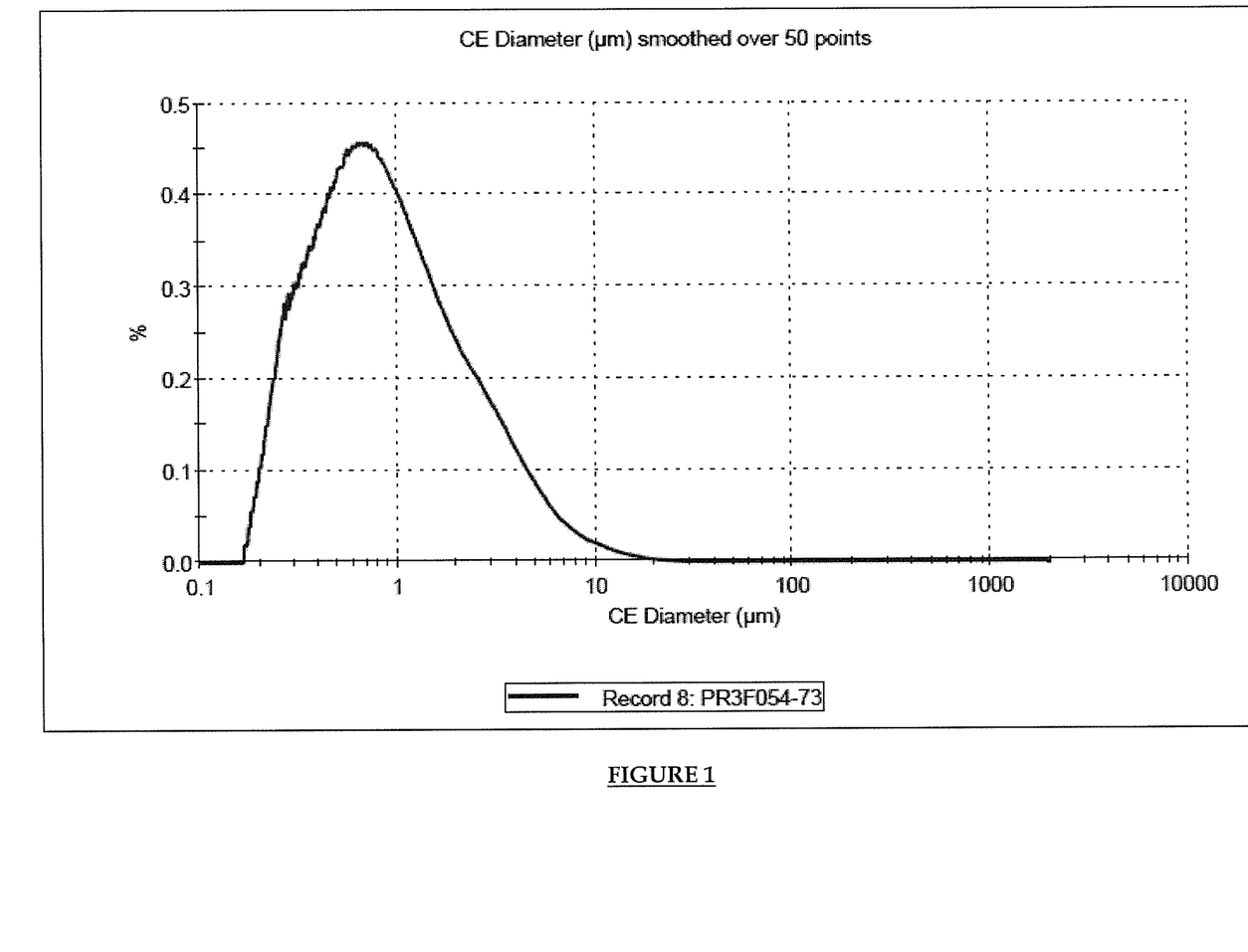
FIG. 1: Showing the particle size evaluation of present invention formulation of brinzolamide ophthalmic suspension 1.0% of batch prepared with homogenization using Morphology G3 instrument from Malvern at Aimil Labs in Delhi.
Figure 2:
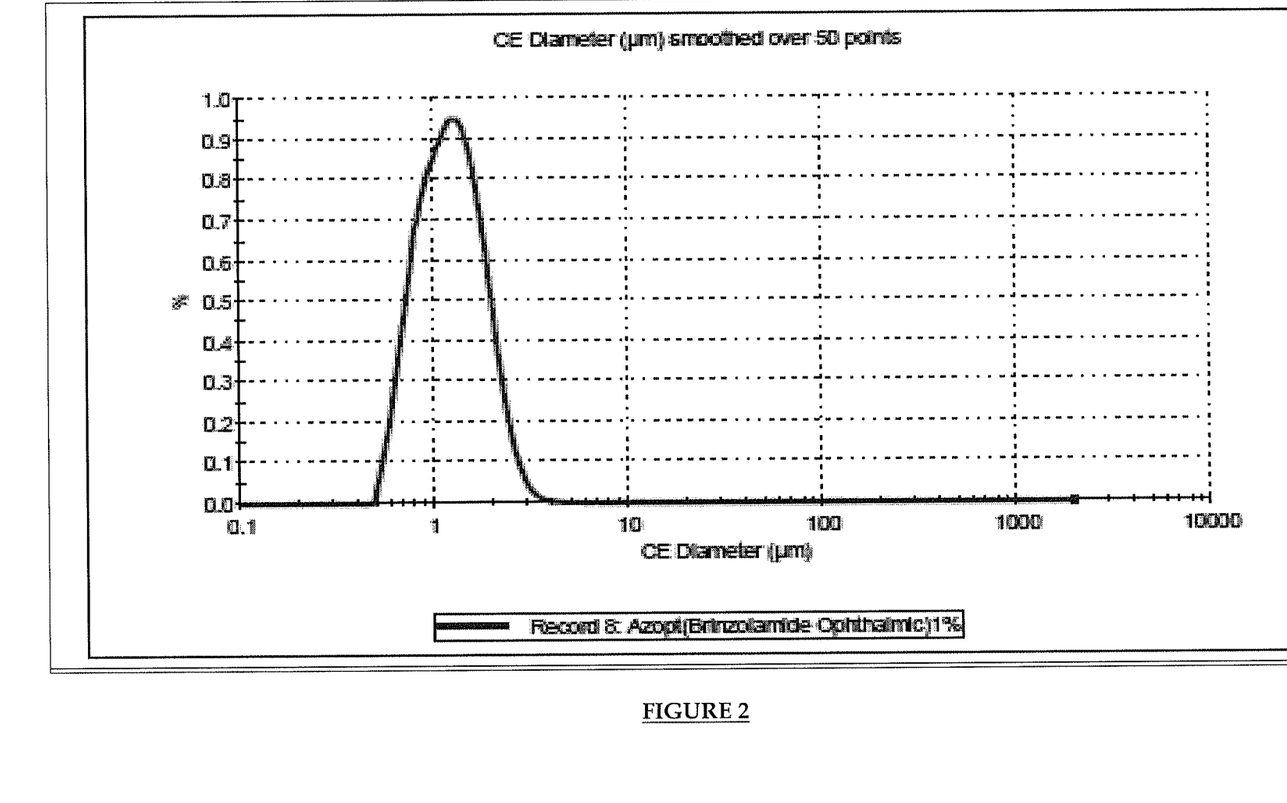
FIG. 2: Showing the particle size evaluation of Reference listed drug (AZOPT®) using Morphology G3 instrument from Malvern at Aimil Labs in Vadodara.
Figure 3:
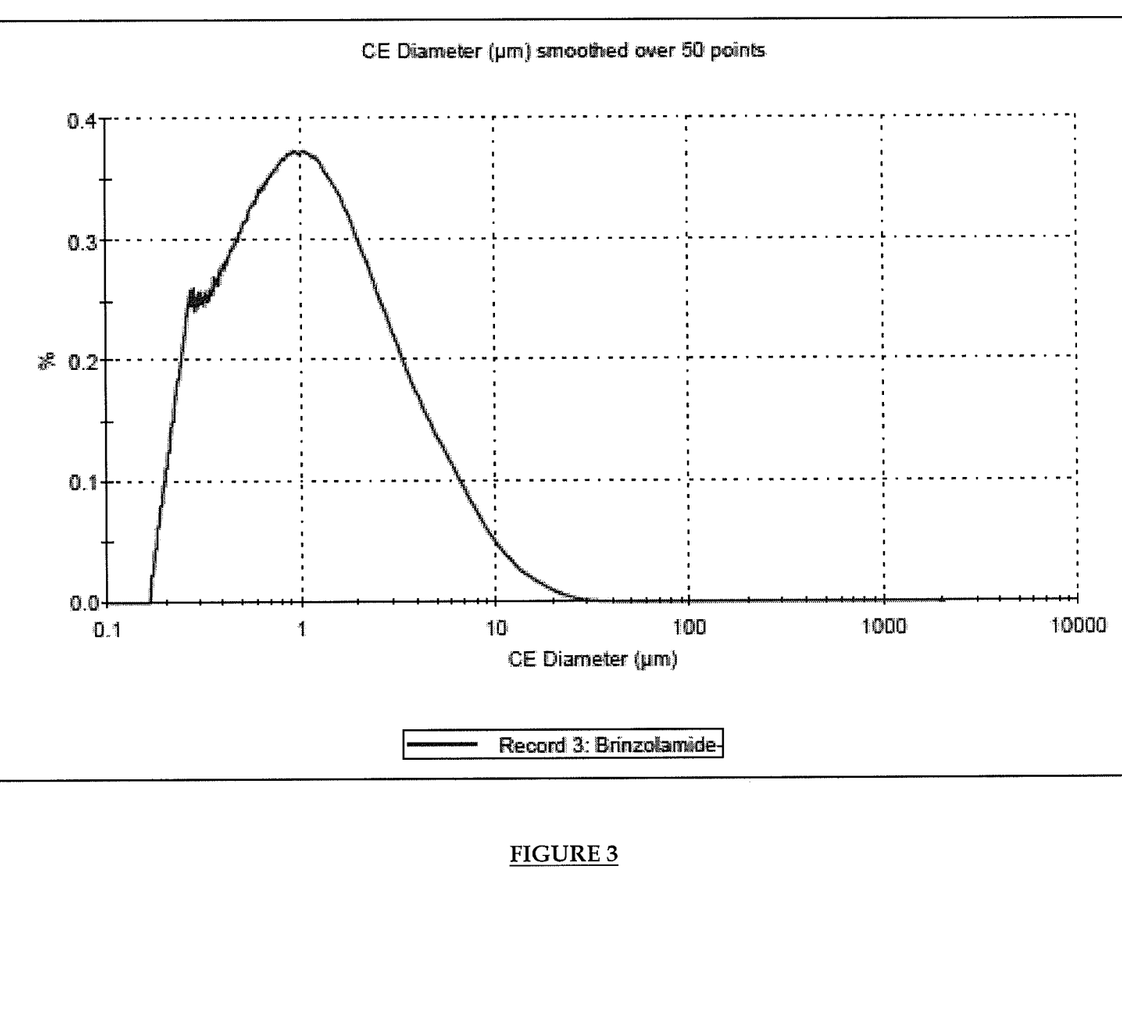
FIG. 3: Showing the particle size evaluation of present invention formulation of brinzolamide ophthalmic suspension 1.0% of batch prepared without homogenization using Morphology G3 instrument from Malvern at Aimil Labs in Delhi.

As used herein, the term "BAC" wherever appears is an abbreviation for "benzalkonium chloride".

As used herein, the "CAIs" wherever appears is an abbreviation for "carbonic anhydrase inhibitors".

As used herein, the "brinzoalmide API" wherever appears is a brinzolamide such as can be procured from ICROM S.p.A, Italy.

As used herein, the "API" wherever appears is an abbreviation for "active pharmaceutical ingredient".

As used herein, the "USP" wherever appears is an abbreviation for "United States Pharmacopeia".

As used herein, the "LDPE" wherever appears is an abbreviation for "low density polyethylene".

As used herein, the "HDPE" wherever appears is an abbreviation for "high density polyethylene".

As used herein, the "BKC" wherever appears is an abbreviation for "benzalkonium chloride".

As used herein, the "NaOH" wherever appears is an abbreviation for "Sodium Hydroxide".

As used herein, the "HCl" wherever appears is an abbreviation for "Hydrochloric Acid".

As used herein, the "EDTA" wherever appears is an abbreviation for "edetate disodium". As used herein, the "RLD" wherever appears is an abbreviation for "Reference listed drug" as developed and marketed by Alcon Laboratories Inc. in United States under the brand name AZOPT® (brinzolamide ophthalmic suspension 1%).

As used herein, wherever the drug comprises brinzolamide, the impurities preferably measured include Impurity A (S)-4-(ethylamino)-3,4-dihydro-2-(3-methoxypropyl)-2H-thieno[3,2-e]-1,2-thiazine-6-sulfonamide 1,1-dioxide; Impurity B, (R)-4-(amino)-3,4-dihydro-2-(3-methoxypropyl)-2H-thieno[3,2-e]-1,2-thiazine-6-sulfonamide 1,1-dioxide, Impurity C (S)-4-(hydroxy)-3,4-dihydro-2-(3-methoxypropyl)-2H-thieno[3,2-e]-1,2-thiazine-6-sulfonamide 1,1-dioxide and Impurity D 6-(amino-hydroxy-oxo-6-sulfanyl)-2-(3-methoxypropyl)-1,1-dioxo-3H-thieno[3,2-e]thiazin-4-one. As used herein, the "active ingredient" is defined as the chemical substance, which is used in the prevention or treatment of various diseases associated with human or non-human animals.

As used herein, the term "Milli Q" water refers to 'ultrapure' water of "Type 1," as defined by various authorities (e.g. ISO 3696).

The present invention relates to an improved novel process of manufacturing a sterile ophthalmic pharmaceutical suspension of non-sterile active ingredient(s) such as non-sterile carbonic anhydrase inhibitor (CAI) or combinations thereof wherein the said novel process involves solubilization, followed by controlled precipitation of brinzolamide of the right particle size, i.e., less than 10 micron, preferably less than 5 micron ($D_{90}$) by varying pH with a little or no homogenization.

The sterile ophthalmic pharmaceutical suspension of the present invention preferably comprises an effective amount of a CAI, the CAI preferably comprising or consisting of brinzolamide or a salt or ester thereof. An effective amount of CAI (e.g., brinzolamide), which can be determined by one of ordinary skill in the art, includes 0.1-5 wt %, preferably 0.5-2 wt %, preferably about 1 wt %, based on weight of CAI free base (e.g., brinzolamide free base). When a beta-blocker is included, the composition preferably comprises an effective amount of beta blocker, which effective amount can be determined by one of ordinary skill in the art.

The term non-sterile active ingredient(s) can be interchangeably used with their pharmaceutically acceptable salt(s), hydrate(s), solvate(s), polymorph(s), stereoisomers), ester(s), prodrug(s), complex(es) and their metabolites thereof.

According to one embodiment of the present invention there is provided a sterile ophthalmic suspension prepared by an improved novel process as described herein comprising non-sterile brinzolamide in an amount from 0.001% to 5.0% by weight.

In an embodiment of the present invention there is provided an improved novel process of manufacturing a sterile ophthalmic suspension wherein the process mainly comprises four stages:
A. Preparation of Remaining Product Vehicle (RPV)
B. Preparation of sterile Milli Q Water
C. Preparation of API Slurry of Correct Particle size (by pH manipulation)
D. Bulk preparation A. Preparation of Remaining Product Vehicle (RPV)
1) Take 60% (of actual batch size) of milli Q water in a clean glass beaker.
2) Add slowly dispensed quantity of disodium edetate followed by mannitol under continuous stirring (rpm 800±100).
3) Slowly add dispensed quantity of carbomer into the above solution at increased rpm (2000±100) via sprinkling. Decrease the stirring rate to 1200±100 after complete addition.
4) After the carbomer has dissolved completely add dispensed quantity of sodium chloride followed by benzalkonium chloride under continuous stirring and stir till the solution is clear.
5) Check the initial pH of the solution, and adjust the pH to 7.5 with 5 N sodium hydroxide solution.
6) Make up the volume with milli Q water up to 80% (of actual batch size).
7) Filter the bulk solution through 47 mm, 20 micron PP filters.
8) Autoclave the RPV at 121° C. for 30 min in a Schott glass bottle.
Note: About 10% RPV excess is prepared to compensate the loss of RPV during filtration and autoclaving. Please note the formulation is stating the exact quantities. However, dispensed quantities will be in 10% excess.

B. Preparation of Sterile Milli Q Water
1) In a Schott glass bottle autoclave enough water that will comprise 20% of total weight of the product. This can be autoclaved in a separate bottle, while autoclaving RPV. Autoclaving to be done at 121° C. for 30 min.

C. Preparation of API Slurry of Correct Particle Size (by pH Manipulation)
1) Take 10% (of actual batch size) of 0.25% tyloxapol solution added in a clean glass beaker, optionally with a beta blocker.
2) Add slowly dispensed quantity of non-sterile API (brinzolamide) to it under continuous stirring.
3) Decrease the pH of the slurry to approximately 2.5 to 3.5 with 5N hydrochloric acid till the API dissolves completely.
4) Filter through 47 mm, 0.22 micron PES filter into a large sterile container under laminar flow hood.
5) Adjust the pH of the API solution to 4.0 to 5.0 with 5 N NaOH solution filtered through sterilizing grade filter so that the API precipitates out. The API will precipitate out as fine particulate matter, ready to be used as ophthalmic suspension. This slurry can be optionally homogenized at 1000±200 bar pressure for 1 to 3 cycles.

D. Bulk Preparation
1) Add the API slurry to previously autoclaved RPV which is approximately 70% of batch size by weight.
2) Make up the volume with previously sterilized milli Q water up to 100.0% (of actual batch size)
3) Stir the solution for 2 hours in aseptic conditions.
4) Fill the final suspension aseptically in previously sterilized bottles, suitable for ophthalmic use.

In the prior art, when brinzolamide precipitates after autoclaving, brinzolamide precipitates as large needle shaped crystals that are several mm to cm long. The inventors of the present invention have surprisingly found that when brinzolamide precipitates due to pH change, it precipitates as very fine crystals, that require little or no homogenization.

In an embodiment of the present invention, this improved novel process involves controlled precipitation by varying pH, and optional use of mild homogenization. Sterilization of the brinzolamide is preferably done by sterile filtration, though other methods may also be used.

Another embodiment of the present invention is to provide an improved novel process for the preparation of sterile brinzolamide ophthalmic suspension. The process being efficient, economic, and feasible for commercial scale preparation and wherein the said process as disclosed herein does not require the use of any special equipment such as ball mill, milling bottle and/or jet mill used in the references (though such may be optionally used without going beyond the scope of the present invention).

In another embodiment, the present invention provides an improved process of manufacturing a sterile brinzolamide ophthalmic pharmaceutical suspension which ameliorates one or more drawbacks of the cited references processes.

The sterile ophthalmic pharmaceutical suspensions as prepared by the novel process of the present invention as disclosed herein the specification are useful in the treatment of elevated intraocular pressure in patients with ocular hypertension or open-angle glaucoma.

In one of the preferred embodiment, the present invention optionally uses approximately only $1/10^{th}$ of the batch volume for high pressure homogenization at pressure 1000±200 bar whereas it is believed that Alcon's process uses the entire batch for ball milling. Thus the process of present invention leads to the minimal wastage of batch product. Also there are reduced or no viscosity issues in the product of present invention with the use of carbomer which further leads to easily homogenizable product which is easy to process and handle.

According to a preferred embodiment, the present invention provides a sterile brinzolamide ophthalmic suspensions comprising: the non-sterile active ingredient brinzolamide, Tyloxapol®; Carbomer® 974 P; mannitol, sodium chloride, edetate disodium, benzalkonium chloride, sodium hydroxide and/or hydrochloric acid (to adjust the pH) wherein the process does not require the use of any special equipment such as ball mill, milling bottle and/or jet mill.

According to a another preferred embodiment, the present invention provides a sterile ophthalmic suspensions comprising: the non-sterile active ingredient brinzolamide, Tyloxapol®; Carbomer® 974 P; mannitol, sodium chloride, edetate disodium, sodium hydroxide and/or hydrochloric acid (to adjust the pH) wherein the process does not require the use of any special equipment such as ball mill, milling bottle and/or jet mill.

The active ingredient used in the present pharmaceutical ophthalmic suspension, may be a soluble or sparingly soluble or slightly soluble or very slightly soluble or practically insoluble compound(s) selected from the group but are not limited to a carbonic anhydrase inhibitor (CAI), such as brinzolamide, acetazolamide, dorzolamide, methazolamide; a beta-blocker, such as timolol, ateolol, metopranolol, betaxolol or other actives used for ophthalmic formulation or a pharmaceutically acceptable salt(s), hydrate(s), solvate(s), polymorph(s), stereoisomers), ester(s), prodrug(s), complex(es) and their metabolites thereof. One of the preferred active is a CAI, or a beta-blocker or a steroid. In a preferred embodiment, the CAI is brinzolamide which is non-sterile in nature, can be in combination with a beta-blocker.

Brinzolamide API used in the preparation of pharmaceutical suspension of the present invention is a sterile or non-sterile (preferably non-sterile) brinzolamide such as can be procured from ICROM S.p.A, Italy.

Examples of polymers that may be used according to the invention include, but are not limited to Carbomer homopolymers Type B such as Carbomer® 974 P (also known as Carbopol® 974P), a synthetic, high molecular weight cross-linked polymer of acrylic acid), povidone, hydroxypropylmethylcellulose, hydroxypropylcellulose, hydroxyethylcellulose and mixtures thereof. Polymers may be used in amount from about 0.1% to about 5.0%, preferably from about 0.3% to about 1.0%.

Examples of preservatives that may be used according to the invention include but are not limited to quaternary ammonium salts such as benzalkonium chloride (BKC) and benzethonium chloride; cationic compounds such as chlorhexidine gluconate; p-hydroxybenzoates such as methyl p-hydroxybenzoate, ethyl p-hydroxybenzoate, propyl p-hydroxybenzoate and butyl p-hydroxybenzoate; alcohol compounds such as chlorobutanol and benzyl alcohol; sodium dehydroacetate; and thiomersal, benzethonium chloride, phenyl ethanol, phenyl propanol, phenyl mercuric acetate, phenyl mercuric nitrate, phenyl mercuric borate, chlorhexidine acetate or gluconate, cetrimide, chlorocresol, sodium methyl paraben, sodiumpropyl paraben, thimerosal, benzalkonium chloride and mixtures thereof and may be used in an amount from about 0.001% to about 0.5%, preferably from about 0.005% to about 0.05%. Of the recited preservatives, quaternary ammonium salts and cationic compounds are preferable as they suppress formation of agglomerates, prevent lowering of pH, and/or provide a suspension superior in redispersibility and stability. Of the quaternary ammonium salts, benzalkonium chloride and benzethonium chloride are particularly preferable, and chlorhexidine gluconate is particularly preferable as the cationic compound.

Examples of surfactants that may be used according to the invention include but are not limited to Tyloxapol®, Triton X-100®, polysorbates, polyoxyl 35 castor oil, polyoxyl 40 hydrogenated castor oil, polyoxyl 40 stearates, sorbitan monolaureates, poloxamer and mixtures thereof and may be used in amount from about 0.001% to about 15%, preferably from about 0.01% to about 0.5%. Tyloxapol® is chemically known as 4-(1,1,3,3-Tetramethylbutyl)phenol polymer with formaldehyde and oxirane. Triton X-100® is chemically known as (a-[4-(1,1,3,3-tetramethylbutyl)phenyl]-co-hydroxypolyoxy-1,2-ethane diyl).

The surfactants used in the pharmaceutical ophthalmic suspension for enhancing dispersion stability preferably include nonionic surfactant(s). The nonionic surfactant to be used is nontoxic, non-irritant and applicable to the eye. Non-limiting examples of the nonionic surfactant include but are not limited to polymer of the alkyl aryl polyether alcohol like tyloxapol; polyoxyethylene polyoxypropylene polymer like triton X-100; polyoxyethylenesorbitan fatty acid esters such as polyoxyethylenesorbitan monooleate, polyoxyethylenesorbitan monolaurate, polyoxyethylenesorbitan monopalmitate and polyoxyethylenesorbitan monostearate; polyoxyethylene hydrogenated castor oils; sorbitan fatty acid esters such as sorbitan monooleate, sorbitan monolaurate, sorbitan monopalmitate and sorbitan monostearate; polyoxyethylene alkyl ethers such as polyoxyethylene lauryl ether; and polyoxyethylene fatty acid esters such as polyoxyethylene monostearate and mixtures thereof. Of the recited nonionic surfactants, alkyl aryl polyether alcohol like tyloxapol, polyoxyethylene polyoxypropylene polymer like triton X-100 are preferable, since they suppress formation of agglomerates, prevent lowering of pH, and provide a suspension superior in redispersibility and stability. The nonionic surfactant is generally contained in a proportion of from about 0.005 w/v % to about 1.0 w/v %, preferably from about 0.01 to about 0.5 w/v % and more preferably from about 0.05 w/v % to about 0.3 w/v % relative to the entire suspension.

Examples of tonicity agents that may be used according to the invention include but are not limited to mannitol, dextrose, glycerin, potassium chloride, sodium chloride and mixtures thereof. The tonizing agent is added in such an amount that makes the osmotic pressure of the suspension identical to that of tears, preferably tonicity agents may be used in amount from about 1% to about 5%.

The pharmaceutical ophthalmic suspension may further include a buffer. The buffer should have buffering capacity in the range of pH from about 5.0 to about 9.0. Examples of the buffer include but are not limited to acetates such as sodium acetate; phosphates such as sodium dihydrogenphosphate, disodium hydrogenphosphate, potassium dihydrogenphosphate and dipotassium hydrogenphosphate; .epsilon.-aminocaproic acid; amino acid salts such as sodium glutamate; and boric acid and a salt thereof. Of the mentioned buffers, acetates and .epsilon.-aminocaproic acid are preferable as they suppress formation of agglomerates, prevent lowering of pH, and provide a suspension superior in re-dispersibility and stability. The buffer is generally contained in a proportion of form about 0.01 w/v % to about 2.0 w/v %, preferably form about 0.05 w/v % to about 0.5 w/v % relative to the entire suspension.

Examples of the pH adjusting agent include but are not limited to hydrochloric acid, citric acid, phosphoric acid, acetic acid, tartaric acid, sodium hydroxide, potassium hydroxide, sodium carbonate and sodium hydrogen carbonate. The pharmaceutical ophthalmic suspension is generally adjusted to pH from about 5.0 to about 9.0, the range which is less irritating to the mucosal membrane of the eye.

Suitable chelating agents/preservative aids includes but are not limited to edetate disodium, edetate trisodium, edetate tetrasodium, diethyleneamine pentaacetate and mixtures thereof. Most preferred is edetate disodium. The chelating agent is generally present in an amount from about 0.001 w/v % to about 0.1 w/v % relative to the entire suspension. In the case of edetate disodium, the chelating agent is preferably present at a concentration of from about 0.005 w/v % to about 0.05 w/v % relative to the entire suspension.

Examples of the antioxidant include but are not limited to ascorbic acid, sodium ascorbate, tocopherol and sulfite salts like sodium sulfite, potassium sulfite, magnesium sulfite, calcium sulfite, sodium bisulfite, potassium bisulfite, magnesium bisulfite, calcium bisulfite, sodium metabisulfite, potassium metabisulfite, calcium metabisulfite, sodium thiosulfate and sodium hydrogensulfite. The sulfite salt is generally being present in an amount from about 0.01 w/v % to about 1% w/v % relative to the entire suspension.

The average particle size of the dispersed or the suspended active is generally from about 0.01μ to about 50μ, preferably from about 0.01μ to about 30μ, more preferably from about 0.1μ to about 20μ and most preferably from about 0.1μ to about 5.0μ. The use of the active in this particle size range affords a suspension having superior dispersibility, which is less irritating to the mucosal membrane of the eye.

Any pharmaceutically acceptable packaging material may be used, preferably packaging material that is suitable for containing ophthalmic pharmaceutical suspensions.

The ophthalmic pharmaceutical suspension is preferably sterile and is filled in a container which is preferably sterile, preferably at the time the container is filled. The ophthalmic pharmaceutical suspension is preferably filled into sterile multi-use or single-use containers.

Pharmaceutically acceptable packaging materials include but are not limited to low density polyethylene ("LDPE"), high density polyethylene ("HDPE"), polypropylene, polystyrene, polycarbonate, polyesters (such as polyethylene terephthalate and polyethylene naphthalate), nylon, poly(vinyl chloride), poly(vinylidine chloride), poly(tetrafluoroethylene) and other materials known to those of ordinary skill in the art. Flexible bottles prepared from, or comprising, LDPE, HDPE or polypropylene are particularly preferred.

In another embodiment, the present invention provides, an improved novel process for manufacturing an ophthalmic suspension comprising an active ingredient such as carbonic anhydrase inhibitors (CAIs) wherein the said process requires little or no homogenization of carbonic anhydrase inhibitors to achieve the desired particle size.

In yet another embodiment, the present invention provides an improved novel process for manufacturing an ophthalmic suspension wherein with the said disclosed process, the present inventors has achieved the desired particle size, irrespective of any sized starting material i.e the actives may be even needle shaped.

In another embodiment of the present invention, the homogenized ophthalmic suspension of non-sterile brinzolamide prepared according to the process as described herein may be filled in three piece low density polyethylene bottle (LDPE), of suitable capacity in volumes of 2.5 ml, 5 ml, 10 ml and 15 ml plugged with natural (LDPE) nozzle and seal with orange colored high density polyethylene (HDPE) cap.

Any suitable method can be used to sterilize the containers, and can be determined by the person of ordinary skill in the art. Some preferred methods include exposure to gamma irradiation and/or exposure to ethylene oxide gas.

The present invention provides a method of using the ophthalmic pharmaceutical formulation prepared according to the process as described herein for treating ocular hypertension and glaucoma. The preferred active ingredient includes but are not limited to the active which is useful in the treatment or prevention of diseases associated to eye like elevated intraocular pressure in patients with ocular hypertension or open-angle glaucoma, ocular surface pain, uveitis, scleritis, episcleritis, keratitis, surgically-induced inflammation, endophthalmitis, iritis, atrophic macular degeneration, retinitis pigmentosa, iatrogenic retinopathy, retinal tears and holes, cystoid macular edema, diabetic macular edema, diabetic retinopathy, sickle cell retinopathy, retinal vein and artery occlusion, optic neuropathy, exudative macular degeneration, neovascular glaucoma, corneal neovascularization, cyclitis, sickle cell retinopathy, pterygium, seasonal allergic conjunctivitis, palpebral and bulbar conjunctiva, acne rosacea, superficial punctuate keratitis, herpes zoster keratitis, iritis, cyclitis, selected infective conjunctivitides, post-operative inflammation following ocular surgery.

The main embodiment of the present invention provides, an improved novel process for manufacturing an ophthalmic suspension comprising an active ingredient such as carbonic anhydrase inhibitors (CAIs) wherein the said process involves solubilization, followed by controlled precipitation of carbonic anhydrase inhibitors of the right particle size, e.g., less than 20 microns, less than 10 microns, preferably less than 5 micron ($D_{90}$), by varying pH with a little or no homogenization.

In another embodiment of the present invention as described above wherein the carbonic anhydrase inhibitor is brinzolamide, preferably non-sterile brinzolamide.

In another embodiment of the present invention as described above wherein the said process is characterized in that it doesn't involve the use of any special equipment such as ball mill, milling bottle and/or, jet mill to achieve desired particle size of brinzolamide.

In another preferred embodiment, the present invention provides an improved process for manufacturing a sterile ophthalmic suspension, the process comprising the steps of:
  (a) preparing sterile suspension vehicle comprising polymer, tonicity agent and preservative; wherein sterile suspension vehicle is achieved by autoclaving at 121° C. in 30 min.
  (b) preparing the API slurry containing surfactant at pH 5.5 to 7.0.
  (c) preparing aqueous solution of Brinzolamide containing surfactant by reducing the pH of API slurry of step (b) to 2.5 to 3.5 from pH 5.5 to 7.0 using 5N HCl;
  (d) aseptically filtering said Brinzolamide solution of step (c);
  (e) precipitating Brinzolamide from the solution of step (d) to form a slurry by raising the pH in a range of 4.0 to 5.0;
  (f) optionally homogenizing said slurry of step (c) comprising Brinzolamide and surfactant;
  (g) aseptically transferring said slurry of step (f) to sterile suspension vehicle of step (a) to obtain a suspension and making up the volume with water.

In another preferred embodiment of the present invention as described above, the said process is characterized in that it doesn't involve the use of any special equipment such as ball mill, milling bottle and/or, jet mill to achieve desired particle size.

In another preferred embodiment of the present invention as described above, homogenization is carried out by using high pressure homogenization at pressure 1000±200 bar to achieve size reduction of the active ingredient Brinzolamide such that the average particle size of brinzolamide is less than about 10 micron, preferably less than about 5 micron ($D_{90}$).

In another preferred embodiment of the present invention as described above, said aseptic filtration is carried out using Polyethersulphone (PES) filters having pore size of about 0.22 microns.

In yet another preferred embodiment, the present invention provides a novel process for manufacturing a sterile ophthalmic suspension, the process comprising:
  (a) preparing a surfactant solution;
  (b) adding Brinzolamide to the said surfactant solution to form an API slurry at pH 5.5 to 7.0;
  (c) preparing aqueous solution of Brinzolamide using hydrochloric acid solution (5N) at pH 2.5 to 3.5;
  (d) aseptically filtering said Brinzolamide solution containing surfactant;
  (e) precipitating Brinzolamide from the solution of step (d) using filtered sodium hydroxide solution (5N), to form a slurry comprising Brinzolamide and surfactant at pH 4.0 to 5.0;
  (f) optionally homogenization of said slurry comprising Brinzolamide and surfactant;
  (g) preparing a viscous suspension vehicle comprising tonicity agent, polymer and preservative and autoclave it after passing through clarifying filter of 20 microns.
  (h) aseptically transferring Brinzolamide slurry of step (f) to the said suspension vehicle of step (g) to obtain a final suspension product.

In yet another preferred embodiment, the present invention provides a novel process for manufacturing a sterile ophthalmic suspension, the process comprising:
  (a) preparing a solution of surfactant and beta-blocker;
  (b) adding Brinzolamide to the said surfactant solution to form an API slurry at pH 5.5 to 7.0;
  (c) preparing aqueous solution of Brinzolamide using hydrochloric acid solution (5N) at pH 2.5 to 3.5;
  (d) aseptically filtering said Brinzolamide solution containing surfactant;
  (e) precipitating Brinzolamide from the solution of step (d) using filtered sodium hydroxide solution (5N), to form a slurry comprising Brinzolamide and surfactant at pH 4.0 to 5.0;
  (f) optionally homogenization of said slurry comprising Brinzolamide and surfactant;
  (g) preparing a viscous suspension vehicle comprising tonicity agent, polymer and preservative and autoclave it after passing through clarifying filter of 20 microns.
  (h) aseptically transferring Brinzolamide slurry of step (f) to the said suspension vehicle of step (g) to obtain a final suspension product.

In another embodiment of the present invention as described above, the ophthalmic pharmaceutical suspension as disclosed herein, upon storage for one month at 40° C./25% RH, or storage for one month at 50° C., comprises less than 0.5 w/v % of Impurity A (S)-4-(ethylamino)-3,4-dihydro-2-(3-methoxypropyl)-2H-thieno[3,2-e]-1,2-thiazine-6-sulfonamide 1,1-dioxide.

In another embodiment of the present invention as described above, the surfactant is selected from the group consisting of Tyloxapol®, Triton X-100®, polysorbates, polyoxyl 35 castor oil, polyoxyl 40 hydrogenated castor oil, polyoxyl 40 stearates, sorbitan monolaureates, poloxamer and combinations thereof.

In another embodiment of the present invention as described above, the polymer is selected from the group consisting of Carbomer®, povidone, hydroxypropyl methyl cellulose, hydroxypropyl cellulose, hydroxyethyl cellulose and combinations thereof.

In another embodiment of the present invention as described above, the preservative is selected from the group consisting of benzethonium chloride, phenyl ethanol, phenyl propanol, phenyl mercuric acetate, phenyl mercuric nitrate, phenyl mercuric borate, chlorhexidine acetate or gluconate, cetrimide, chlorocresol, sodium methyl paraben, sodiumpropyl paraben, thimerosal, benzalkonium chloride and combinations thereof.

In another embodiment of the present invention as described above, the tonicity agent is selected from the group consisting of mannitol, dextrose, glycerin, potassium chloride, sodium chloride and combinations thereof.

In another embodiment of the present invention as described above, the chelating agents/preservative aid if used, include edetate disodium, edetate trisodium, edetate tetrasodium, diethyleneamine pentaacetate and combinations thereof.

In another embodiment of the present invention as described above, the ophthalmic pharmaceutical suspension as disclosed herein is stable when stored for 1 month at 40° C. at no more than 25% relative humidity.

In another embodiment of the present invention as described above, the ophthalmic suspension is packaged in a multi dose container.

In another embodiment of the present invention as described above, the ophthalmic suspension is packaged in a unit dose container.

In another embodiment of the present invention as described above, is included a method of treating elevated intraocular pressure in persons suffering from ocular hypertension or primary open angle glaucoma, comprising applying at least once a day to an eye of a patient in need thereof a composition of the present invention. In another embodiment of the present invention as described above, the applying of said ophthalmic pharmaceutical suspension is done twice a day. In another embodiment of the present invention as described above, the applying of said ophthalmic pharmaceutical suspension is once a day.

Stability Studies:

A sterile, ophthalmic pharmaceutical suspension of the present invention is prepared by the process described herein in the specification and is tested for stability against a control product (herein referred to as "AZOPT®," approved by the U.S. FDA under NDA NO20816). One month stress testing refers to storage at 50° C. One month accelerated testing refers to storage at 40° C., at not more than (and preferably at) 25% relative humidity (RH). Results for one (1) month both at stress and accelerated testing for both the control product (herein referred to as "AZOPT®") and the present invention formulation are provided in Table 1.

An accelerated study comprises placing the composition/suspension is filled in 10 mL 3 piece natural LDPE bottles, natural LDPE nozzle and orange colored cap. (Sterilized by ETO gas Sterilization) and maintaining at 40° C., at not more than 25% relative humidity (RH) in the dark.

As understood by those of skill in the art, when the drug comprises brinzolamide, the impurities preferably measured include Impurity A (S)-4-(ethylamino)-3,4-dihydro-2-(3-methoxypropyl)-2H-thieno[3,2-e]-1,2-thiazine-6-sulfonamide 1,1-dioxide; Impurity B, (R)-4-(amino)-3,4-dihydro-2-(3-methoxypropyl)-2H-thieno[3,2-e]-1,2-thiazine-6-sulfonamide 1,1-dioxide, Impurity C (S)-4-(hydroxy)-3,4-dihydro-2-(3-methoxypropyl)-2H-thieno[3,2-e]-1,2-thiazine-6-sulfonamide 1,1-dioxide and Impurity D 6-(amino-hydroxy-oxo-6-sulfanyl)-2-(3-methoxypropyl)-1, 1-dioxo-3H-thieno[3,2-e]thiazin-4-one and total impurities, as well as identification of the amount of the any independent unspecified impurity.

TABLE 1

Comparative Stability Data of "Reference listed drug" AZOPT(R) and present invention formulation.

| Batch No. Assay | Release Specifications | Initial | Shelf life Specifications | 40° C./25% RH 1 Month | 50° C. 4 W |
|---|---|---|---|---|---|
| RLD (AZOPT(R)) B. No. 231374F | 93.0-107.0% of labeled amount | 97.3% | 90.0-110.0% of labeled amount | 99.6% | 102.6% |
| PR3F054-73 | | 102.3% | | 99.8% | 100.7% |
| Impurity Related compound A (Impurity A) | | | | | |
| RLD (AZOPT(R)) B. No. 231374F | NMT 1.0% | 0.75% | NMT 1.5% | 0.93% | 1.38% |
| PR3F054-73 | | 0.01% | | 0.05% | 0.48% |
| Related compound B (Impurity B) | | | | | |
| RLD (AZOPT(R)) B. No. 231374F | NMT 0.4% | 0.05% | NMT 0.5% | 0.04% | 0.04% |
| PR3F054-73 | | ND | | 0.01% | 0.01% |
| Related compound D (Impurity D) | | | | | |
| RLD (AZOPT(R)) B. No. 231374F | NMT 0.4% | 0.01% | NMT 0.5% | ND | ND |
| PR3F054-73 | | ND | | ND | ND |
| Any individual impurity | | | | | |
| RLD (AZOPT(R)) B. No. 231374F | NMT 0.4% | NA | NMT 0.5% | NA | NA |
| PR3F054-73 | | ND | | BDL | ND |
| Total impurities | | | | | |
| RLD (AZOPT(R)) B. No. 231374F | NMT 1.0% | 0.06% | NMT 2.0% | 0.04% | 0.1% |
| PR3F054-73 | | 0.01% | | 0.01% | 0.01% |

As used herein, the "NMT" wherever appears is an abbreviation for "Not more than".
As used herein, the "ND" wherever appears is an abbreviation for "Not detected".
As used herein, the "NA" wherever appears is an abbreviation for "Not Applicable" as peak observed in house placebo are not reported in total RS (total related substances).

Details of the Batches:

| Batch No. | Mfg. date/Expiry date | Date of initiation of study |
|---|---|---|
| PR3F054-73 | Mfg. date: Nov 15 | 04 Dec 15 |
| RLD (AZOPT(R)) B. No. 231374F manufactured by Alcon Laboratories Inc. | Exp. Date: May 16 | 19 Sep 14 |

TABLE 2

Comparative data of different lots of RLD from different markets

| | Russia RLD | EU RLD | US RLD | | |
|---|---|---|---|---|---|
| Batch No. | 13F21F | 12F19G | 203411F | 203168F | 231374F |
| Expiry date | Jun 15 | May 14 | Apr 14 | Mar 14 | May 16 |
| Date of analysis | Nov 13 | Nov 13 | May 13 | Nov 13 | Sep 14 |
| Approximate age of the product at the time of analysis | 5 months* | 1.5 years* | 1 year* | 1.7 year* | 4 months* |
| Assay (By HPLC) | 98.90% | 100.50% | 102.00% | 98.58% | 97.30% |
| Related compound A (Impurity A) | 0.86% | 0.60% | 0.90% | 0.91% | 0.75% |
| Impurity B | 0.05% | 0.04% | 0.05% | 0.05% | 0.05% |

TABLE 2-continued

Comparative data of different lots of RLD from different markets

|  | Russia RLD | EU RLD | US RLD | | |
|---|---|---|---|---|---|
| Batch No. | 13F21F | 12F19G | 203411F | 203168F | 231374F |
| Impurity D | ND | ND | ND | ND | 0.01% |
| Total impurity | 0.12% | 0.24% | 0.22% | 0.13% | 0.38% |

*Approximate ages of the commercially-obtained products at the time of analysis are based on an assumed two (2) years of shelf life.

Observations

It is observed from the stability data that due to an improved process, formation of related substance A (Impurity A) at initial time point is much less in present invention formulation than RLD (AZOPT®) due to which its formation over the time at accelerated condition has decreased.

In case of RLD, the impurity A has increased from 0.75% (at initial) to 0.93% over one month at accelerated condition for the RLD, whereas in case of present invention formulation the impurity was 0.01% at initial analysis and has increased to 0.05% over one month at same storage conditions, indicating that the rate of increase of impurity A has decreased tremendously in case of the present invention formulation.

The impurity A of RLD is more than the present invention formulation whether the analysis is done near to the expiry of the RLD or one (1) year before its expiry, as it can be seen from the table that initial assay of impurity A does not correlate well with the age of the product. Without being bound by theory, this supports the statement that manufacturing process is a main contributor for the formation of Impurity A. Impurity A is also formed on storage. However controlling Impurity A by manufacturing process gives a better control over it.

Some other parameters like content of BKC, content of Edetate Disodium, Osmolality, Viscosity, pH and Particle Size are also analyzed and are found to be within specifications and comparable with the RLD.

From the above stability results it can be easily concluded that the present invention formulation complies with the specifications as per USP and in-house specification throughout the study and is comparable with the RLD.

It is also concluded that the present invention formulation is more stable over the period of one month at accelerated condition (40±2° C./25% RH) and stability data is well within the specifications and comparable with the RLD (AZOPT®). Hence the present invention formulation prepared by the improved process is more patient compliant.

Further, it is also concluded that the manufacturing process of the present invention reduces the generation of Impurity A wherein the reduction of Impurity A will enhance the shelf-life of the product thereby increases the stability of the present invention.

Furthermore, the ophthalmic pharmaceutical suspension of the present invention upon storage for one months at 50° C., has 0.48% of Impurity A (S)-4-(ethylamino)-3,4-dihydro-2-(3-methoxypropyl)-2H-thieno[3,2-e]-1,2-thiazine-6-sulfonamide 1,1-dioxide which is far less than the RLD (1.38%).

EXAMPLES

The scope of the present invention is illustrated by the following examples which are not meant to restrict the scope of the invention in any manner whatsoever.

The term 'q.s.' wherever appears in the examples is an abbreviation for 'quantity sufficient' which is the amount of the excipient in such quantities that is just sufficient for its use in the composition of the present invention.

Example 1

| Ingredients | Quantity (%) |
|---|---|
| Brinzolamide | 1 |
| Tyloxapol | 0.025 |
| Carbomer 974P | 0.45 |
| Edetate disodium | 0.01 |
| BKC | 0.01 |
| Mannitol | 3.3 |
| Sodium Chloride | 0.25 |
| NaOH/HCl | q.s. |
| Water for Injection | Up to 100% |

Example 2

| Ingredients | Quantity (%) |
|---|---|
| Brinzolamide | 1.0 |
| Tyloxapol | 0.025 |
| Carbomer 974P | 0.42 |
| Edetate disodium | 0.01 |
| Benzalkonium Chloride | 0.01 |
| Mannitol | 3.3 |
| Sodium chloride | 0.25 |
| Sodium hydroxide/Hydrochloric acid | q.s. |
| Water for Injection | q.s. |

Brief Manufacturing Procedure:

The process for preparation of pharmaceutical ophthalmic suspension shall be divided in following parts.
  A. Remaining product vehicle (solution of EDTA, Mannitol, Carbomer, sodium chloride, Benzalkonium chloride) (37 kg)
  B. Preparation of API Slurry of Correct Particle size (by pH manipulation)
  C. Slurry Homogenization, if required or optionally selected.
  D. Water for injection.

Part A. Remaining Product Vehicle:
  1. Weigh and check the weight of all ingredients.
  2. Take approximately 120% of required quantity of Water for injection in a Manufacturing tank-1
  3. Purge filtered Nitrogen gas and Cool Water for Injection, using cooling jacket to 30° C. (range 25° to 35° C.), through sparger till the dissolved oxygen level reaches to not more than 2 ppm.

4. Transfer 60% of required quantity of cooled water for injection from manufacturing tank-1 to Manufacturing tank-2.
5. Add and dissolve edetate disodium in the Manufacturing tank-2 with continuous stirring.
6. Add and dissolve Mannitol in the Manufacturing tank-2 with continuous stirring
7. Add and dissolve carbomer 974P slowly in the Manufacturing tank-2 with continuous stirring.
8. Add and dissolve sodium chloride in the Manufacturing tank-2 with continuous stirring at RPM 350±50.
9. Add and dissolve diluted Benzalkonium chloride solution in the Manufacturing tank-2 with continuous stirring. Rinse the container multiple times with sufficient water for injection for complete transfer.
10. Adjust the pH of the solution between 7.5±0.3 by adding 5 N Sodium Hydroxide/1N Hydrochloric Acid, in increments, if required. Stir solution for 5 min between each increment.
11. Make up the weight of bulk solution to 50 kg batch.
12. Transfer the above bulk solution from manufacturing tank-2 to filtration tank through 20μ Polypropylene filter. Record the loss during transfer.
13. Sterilize the bulk in filtration tank by in-situ sterilization (30 min, NLT 121.6° C., 1 cycle)

Part B. Preparation of API Slurry of Correct Particle Size (by pH Manipulation).
1. In separate pressure vessel prepare the solution of Tyloxapol by collecting 3-4 L water for injection in pressure vessel and dissolve the dispensed batch quantity in hot water for injection and adding this to pressure vessel.
2. Add slowly dispensed quantity of non-sterile API (brinzolamide) to it under continuous stirring.
3. Decrease the pH of the slurry to approximately 2.5 to 3.5 with 5N hydrochloric acid till the API dissolves completely. Make up the volume to 10% of batch size.
4. Filter through 47 mm, 0.22 micron PES filter into a 15 L tank.
5. Adjust the pH of the API solution to 4.0 to 5.0 with 5 N NaOH solution filtered through sterilizing grade filter so that the API precipitates out.

Part C. Slurry Homogenization, if Required or Optionally Selected.
1. Stir the slurry for not less than 3 hr using magnetic stirrer at sufficient RPM to generate vortex and avoiding high turbulence.
2. Create loop to facilitate the recirculation in homogenization process and its transfer to filtration tank. Homogenize the slurry using high pressure homogenizer at pressure 1000±200 bar (for 50 L batch size)
3. Transfer this homogenized slurry into sterile bulk in filtration tank.
4. Rinse the slurry tanks (15 L tank) with aseptically filtered, approximately 5 L water (Refer Part D for details) and add this rinsate to sterile bulk in filtration tank through homogenizer (at pressure 1000±200 bar)
5. Make the bulk weight considering density 1.016 g/ml in filtration tank using sterile water for injection used in rinsing of 15 L tank.
6. Continue the stirring to get a uniform bulk. Stir it for 2 hr and send the samples for bulk analysis.

Part D: Pre-Sterilized Water for Injection
1. Collect water for injection into manufacturing tank 1, filter it through 0.2μ filter, used for filtering API solution containing tyloxapol & collect in 15 L tank (used for slurry) and use this for volume make up in filtration tank.

Example 3

| Ingredients | Quantity (%) |
| --- | --- |
| Brinzolamide | 1.0 |
| Tyloxapol | 0.025 |
| Carbomer 974P | 0.42 |
| Edetate disodium | 0.01 |
| Mannitol | 3.3 |
| Sodium chloride | 0.25 |
| Sodium hydroxide/Hydrochloric acid | q.s. |
| Water for Injection | q.s. |

Brief Manufacturing Procedure:
The process for preparation of pharmaceutical ophthalmic suspension shall be divided in following parts.
A. Remaining product vehicle (solution of EDTA, Mannitol, Carbomer, sodium chloride)
B. Preparation of API Slurry of Correct Particle size (by pH manipulation)
C. Slurry Homogenization, if required
D. Water for injection.

Part A. Remaining Product Vehicle:
1. Weigh and check the weight of all ingredients.
2. Take approximately 120% of required quantity of Water for injection in a Manufacturing tank-1
3. Purge filtered Nitrogen gas and Cool Water for Injection, using cooling jacket to 30° C. (range 25° to 35° C.), through sparger till the dissolved oxygen level reaches to not more than 2 ppm.
4. Transfer 60% of required quantity of cooled water for injection from manufacturing tank-1 to Manufacturing tank-2.
5. Add and dissolve edetate disodium in the Manufacturing tank-2 with continuous stirring.
6. Add and dissolve Mannitol in the Manufacturing tank-2 with continuous stirring
7. Add and dissolve carbomer 974P slowly in the Manufacturing tank-2 with continuous stirring.
8. Add and dissolve sodium chloride in the Manufacturing tank-2 with continuous stirring at RPM 350±50.
9. Rinse the container multiple times with sufficient water for injection for complete transfer.
10. Adjust the pH of the solution between 7.5±0.3 by adding 5 N Sodium Hydroxide/1N Hydrochloric Acid, in increments, if required. Stir solution for 5 min between each increment.
11. Make up the weight of bulk solution to 50 kg batch.
12. Transfer the above bulk solution from manufacturing tank-2 to filtration tank through 20μ Polypropylene filter. Record the loss during transfer.
13. Sterilize the bulk in filtration tank by in-situ sterilization (30 min, NLT 121.6° C., 1 cycle)

Part B. Preparation of API Slurry of Correct Particle Size (by pH Manipulation).
1. In separate pressure vessel prepare the solution of Tyloxapol by collecting 3-4 L water for injection in pressure vessel and dissolve the dispensed batch quantity in hot water for injection and adding this to pressure vessel.
2. Add slowly dispensed quantity of non-sterile API (brinzolamide) to it under continuous stirring.

3. Decrease the pH of the slurry to approximately 2.5-3.5 with 5N hydrochloric acid till the API dissolves completely. Make up the volume to 10% of batch size.
4. Filter through 47 mm, 0.22 micron PES filter into al 5 L tank.
5. Adjust the pH of the API solution to 4.0-5.0 with 5 N NaOH solution filtered through sterilizing grade filter so that the API precipitates out.

Part C. Slurry Homogenization, if Required.
1. Stir the slurry for not less than 3 hr using magnetic stirrer at sufficient RPM to generate vortex and avoiding high turbulence.
2. Create loop to facilitate the recirculation in homogenization process and its transfer to filtration tank. Homogenize the slurry using high pressure homogenizer at pressure 1000±200 bar (for 50 L batch size)
3. Transfer this homogenized slurry into sterile bulk in filtration tank.
4. Rinse the slurry tanks (15 L tank) with aseptically filtered, approximately 5 L water (Refer Part D for details) and add this rinsate to sterile bulk in filtration tank through homogenizer (at pressure 1000±200 bar)
5. Make the bulk weight considering density 1.016 g/ml in filtration tank using sterile water for injection used in rinsing of 15 L tank.
6. Continue the stirring to get a uniform bulk. Stir it for 2 hr and send the samples for bulk analysis.

Part D. Pre-Sterilized Water for Injection.
1. Collect water for injection into manufacturing tank 1, filter it through 0.2μ filter, used for filtering API solution containing tyloxapol & collect in 15 L tank (used for slurry) and use this for volume make up in filtration tank.

Further the particle size obtained by the present invention process is similar to that of ball milling process as shown in Table 3. However the novel present invention process is much simpler, more efficient and economical as compared to the ball mill process.

For development studies, particle size evaluation has been performed using Morphology G3 instrument from Malvern at Aimil Labs in Delhi as shown in Table 3.

TABLE 3

Comparison of particle size between present invention formulations of brinzolamide ophthalmic suspension 1.0% and Reference listed drug (AZOPT$^{(R)}$)

| Particle size | RLD 203411F | Present Invention | |
|---|---|---|---|
| | | PR3F054-73 (homogenized) | PR3F054-77A (Un-homogenized) |
| Mean Diameter (μm) | 1.29 | 1.4 | 1.93 |
| D(0.9) | 1.89μ | 3.05μ | 4.43μ |
| D(0.5) | 1.21μ | 0.82μ | 1.06μ |
| D(0.1) | 0.75μ | 0.31μ | 0.31μ |

In general, particles <10 μm are recommended for ophthalmic suspension formulations for patient comfort and to minimize damage to cornea besides influencing the rate and extent of dissolution. From the above data it is clear that with this new process, the particle size distribution is <10 μm. So brinzolamide suspension manufactured with this new process without homogenization is suitable for ophthalmic use. This is a surprising and novel finding that brinzolamide precipitated by pH manipulation has the right particle size for ophthalmic use.

Further, the $D_{10}$ & $D_{50}$ values of the product manufactured by this new process are comparable to the innovator's product, Azopt, though it appears that there is slight difference in the particle size w.r.t. $D_{90}$. However, in real sense, it may not make any significant difference, as solubility of brinzolamide is around 0.08% in tear fluid and in the product, concentration of active is 1%. Hence, there will not be any difference in the amount of dissolved drug which is absorbed from solution. The absorbed or diffused drug is replenished by the solubilization of drug from mostly the smallest particle, which is determined by $D_{10}$. It is also interesting to note that the critical $D_{10}$ is same in the batches prepared with and without homogenization though the $D_{50}$ and $D_{90}$ are higher in case of batch prepared without homogenization. This suggests that loose agglomerates are formed in this case which can easily be broken with use of mild sonication, pressure or high shear mixing or use of homogenization, if required.

From the particle size analysis as depicted above in Table 3, it is inferred that present invention formulation of brinzolamide ophthalmic suspension 1.0% is comparable with Reference listed drug i.e. AZOPT®, manufactured by Alcon Pharmaceuticals.

UTILITY OF THE PRESENT INVENTION

The present inventors provides a simpler, cost effective and efficient novel process for manufacturing sterile, ophthalmic pharmaceutical suspension comprising carbonic anhydrase inhibitors (CAIS) wherein the said process involves solubilization, followed by controlled precipitation of carbonic anhydrase inhibitors of the right particle size, i.e., 1 less than 10 micron, preferably less than 5 micron ($D_{90}$) by varying pH with a little or no homogenization.

The prepared suspension according to the disclosed novel process is useful in treatment of elevated intraocular pressure in patients with ocular hypertension or, open angle glaucoma.

We claim:
1. A process for manufacturing an ophthalmic suspension comprising an effective amount of an active ingredient comprising at least one carbonic anhydrase inhibitor (CAI) wherein the process includes solubilizing the at least one CAI, followed by performing controlled precipitation of the at least one CAI by varying pH during the precipitation to obtain a particle size less than 20 microns ($D_{90}$) and not more than 0.4% of any individual impurity.
2. The process as claimed in claim 1, wherein the carbonic anhydrase inhibitor comprises brinzolamide.
3. The process as claimed in claim 1, wherein the process does not include use of a ball mill, a milling bottle, and/or a jet mill to achieve the particle size; and optionally includes mild homogenization.
4. A process for manufacturing a volume of sterile ophthalmic suspension, the process comprising:
   (a) preparing a sterile suspension vehicle comprising a polymer, a tonicity agent and a preservative; wherein a sterile suspension vehicle is achieved by autoclaving;
   (b) preparing an API slurry containing Brinzolamide and a surfactant at pH 5.5 to 6.5;
   (c) preparing an aqueous solution of Brinzolamide containing surfactant by reducing pH of the API slurry to 2.5 to 3.5;
   (d) aseptically filtering said solution of Brinzolamide;
   (e) precipitating Brinzolamide from the solution of (d) to form a slurry by raising the pH to a range of 4.0 to 5.0 to obtain a particle size less than 20 microns (D90), followed by optional homogenization; and (f) aseptically combining said slurry of (e) with the sterile suspension vehicle of (a) to obtain a suspension, and making up the volume with water.

5. The process as claimed in claim 4, wherein the precipitated Brinzolamide in the sterile ophthalmic suspension has a $D_{90}$ of less than 20 microns, which $D_{90}$ is obtained without use of a ball mill, a milling bottle and/or a jet mill.

6. The process as claimed in claim 4, wherein homogenization comprises high pressure homogenization at pressure 1000±200 bar to provide an average particle size of brinzolamide of less than 10 microns.

7. The process as claimed in claim 4, wherein said aseptic filtration comprises filtration with a Polyethersulphone (PES) filter having pore size of about 0.22 microns.

8. A process for manufacturing a sterile ophthalmic suspension, the process comprising:
(a) preparing an aqueous surfactant solution;
(b) adding Brinzolamide to the surfactant solution to form an API slurry;
(c) preparing aqueous solution of Brinzolamide having pH of 2.5 to 3.5, by combining the API slurry with an acid;
(d) aseptically filtering said Brinzolamide solution containing surfactant;
(e) precipitating Brinzolamide by combining the solution of (d) with a base to form a slurry comprising Brinzolamide and surfactant at pH 4.0 to 5.0 to obtain a particle size less than 20 microns (D90), followed by optional homogenization;
(f) preparing a suspension vehicle comprising a tonicity agent, a polymer and a preservative, and autoclaving the suspension vehicle after passing it through a clarifying filter;
(g) aseptically combining the Brinzolamide slurry of (e) with the suspension vehicle of (f).

9. A process for manufacturing a sterile ophthalmic suspension, the process comprising:
(a) preparing a solution of a surfactant and a beta-blocker;
(b) adding Brinzolamide to the surfactant solution to form an API slurry;
(c) preparing an aqueous solution of Brinzolamide by combining the composition of (b) with an acid to obtain a pH of 2.5 to 3.5;
(d) aseptically filtering said Brinzolamide solution of (c);
(e) precipitating Brinzolamide from the solution of (d) using a base, to form a slurry comprising Brinzolamide and surfactant at pH 4.0 to 5.0 to obtain a particle size less than 20 microns (D90), followed by optional homogenization;
(f) preparing a suspension vehicle comprising a tonicity agent, a polymer and a preservative, and autoclaving the suspension vehicle after passing through a clarifying filter;
(g) aseptically combining the Brinzolamide slurry of (e) with the suspension vehicle of (f).

10. The process as claimed in claim 1, wherein the ophthalmic suspension comprises a surfactant selected from the group consisting of an alkyl aryl polyether polymer, an polyoxyethylene polyoxypropylene polymer, polysorbates, polyoxyl 35 castor oil, polyoxyl 40 hydrogenated castor oil, polyoxyl 40 stearates, sorbitan monolaureates, poloxamer and combinations thereof.

11. The process as claimed in claim 1, wherein the ophthalmic suspension comprises a polymer selected from the group consisting of Carbomer, povidone, hydroxypropyl methyl cellulose, hydroxypropyl cellulose, hydroxyethyl cellulose and combinations thereof.

12. The process as claimed in claim 1, wherein the ophthalmic suspension comprises a preservative selected from the group consisting of benzethonium chloride, phenyl ethanol, phenyl propanol, phenyl mercuric acetate, phenyl mercuric nitrate, phenyl mercuric borate, chlorhexidine acetate or gluconate, cetrimide, chlorocresol, sodium methyl paraben, sodiumpropyl paraben, thimerosal, benzalkonium chloride and combinations thereof.

13. The process as claimed in claim 1, wherein the ophthalmic suspension comprises a tonicity agent selected from the group consisting of mannitol, dextrose, glycerin, potassium chloride, sodium chloride and combinations thereof.

14. The process as claimed in claim 1, wherein the ophthalmic suspension comprises a chelating agent selected from the group consisting of edetate disodium, edetate trisodium, edetate tetrasodium, diethyleneamine pentaacetate and combinations thereof.

* * * * *